United States Patent
Riess et al.

(10) Patent No.: US 7,271,388 B2
(45) Date of Patent: Sep. 18, 2007

(54) IDENTIFICATION OF BROMINATED FLAME RETARDANT ADDITIVES IN POLYMERS BY INFRARED SPECTROSCOPY

(75) Inventors: Michael Riess, Taunusstein (DE); Julia Smirnow, Wiesbaden (DE)

(73) Assignee: Motorola, Inc., Schaumburg, IL (US)

( * ) Notice: Subject to any disclaimer, the term of this patent is extended or adjusted under 35 U.S.C. 154(b) by 266 days.

(21) Appl. No.: 10/896,800

(22) Filed: Jul. 22, 2004

(65) Prior Publication Data

US 2006/0017914 A1    Jan. 26, 2006

(51) Int. Cl.
   *G01J 5/02*   (2006.01)
(52) U.S. Cl. ............... 250/341.8; 250/339.11
(58) Field of Classification Search .......... 250/339.13, 250/339.01, 339.11, 341.8
   See application file for complete search history.

(56) References Cited

U.S. PATENT DOCUMENTS

| | | | |
|---|---|---|---|
| 5,448,070 A | | 9/1995 | Day et al. |
| 6,175,111 B1* | | 1/2001 | Sorita et al. ................ 250/282 |
| 6,344,648 B1* | | 2/2002 | Boucher et al. ............ 250/343 |
| 6,555,822 B1* | | 4/2003 | Zoidis ..................... 250/341.1 |
| 6,690,015 B1 | | 2/2004 | Benes et al. |
| 2002/0086928 A1* | | 7/2002 | Ouchi ........................ 524/409 |

OTHER PUBLICATIONS

Becker, Wolfgang et al. "Identification of Brominated Flame Retardants in Plastics". Fraunhofer-Institut für Chemische Technologie. Accessible Online: <http://www.apme.org/media/public_documents/20030508_155207/5_Eisenreich_session%205.pdf>.

* cited by examiner

*Primary Examiner*—David Porta
*Assistant Examiner*—David S. Baker

(57) ABSTRACT

A method for identifying brominated flame retardants in a polymer sample. An infrared spectrometry scan of the polymer sample is obtained. Using a first set of parameters, the obtained IR scan is compared to a first database, and a first hit score is calculated. Based on the results of the first hit score, a second database is selected from among a number of databases, and the obtained infrared spectrometry scan is compared to the various scans contained in the selected database using a parameter set that corresponds to the selected database, and a second hit score is calculated. Using the second hit score, another set of parameters is selected, and the obtained infrared spectrometry scan is compared to the various scans contained in the selected third database using this additional parameter set, and a third hit score is calculated. Based on the second and third hit scores, the identity of the brominated flame retardant in the polymer sample is determined with a high degree of accuracy.

17 Claims, 3 Drawing Sheets

IDENTIFICATION OF BROMINATED FLAME RETARDANT ADDITIVES IN POLYMERS BY INFRARED SPECTROSCOPY

FIELD OF THE INVENTION

This invention relates generally to infrared spectroscopy, and more particularly, to the use of infrared spectroscopy to detect and identify brominated flame retardants in engineering plastics.

BACKGROUND

Brominated flame retardants are used as additives in many engineering plastics to meet current safety standards for flammability. These plastics are commonly used in the industrial and consumer electronics markets for applications such as plastic housings, battery packages, printed circuit boards, adhesives, shrink tubing, etc. Most brominated flame retardants consist of at least one aromatic ring and they all carry a high number of bromine atoms. While they substantially reduce the flammability characteristics of these polymers, brominated flame retardants are regarded as an environmental hazard because they are toxic and/or carcinogenic. They contribute to the formation of dioxins when incinerated or exposed to intense heat during recycling. The various types of flame retardants have different levels of toxicity or contribute differently to the formation of dioxins. Legislation in the European Union (EU) has been enacted to reduce the level of brominated flame retardants in the environment. The Restriction of certain Hazardous Substances (RoHS) act has targeted brominated flame retardants in electronic devices, and provides an outright ban on two types of brominated flame retardants, polybrominated biphenyls (PBB) and polybrominated diphenyl ethers (PBDE).

In order to comply with theses enacted regulations, a method to detect and identify brominated flame retardants in engineering plastics is needed. Such a method should be fast and accurate to enable rapid testing and short turnaround times in keeping with the 'time to market' requirements of the global electronics industry. The detection method also needs to be highly cost effective and it should not have any adverse impact on the environment by using other hazardous substances in the detection procedure, and it should be easy to use.

Historically, a number of methods have been used in the chemical laboratory to determine the presence of additives in polymers, such as high pressure liquid chromatography (HPLC), gas chromatography/mass spectral analysis (GC-MS), laser thermography, laser plasma emission, x-ray fluorescence, pyrolysis, and infrared (IR) spectroscopy techniques such as multiple internal reflectance (MIR), Raman scattering, and near infrared. Some of these techniques have been used with varying degrees of success in the analysis of brominated flame retardants in polymers. The HPLC detection method, for example, requires a number of sample preparation steps and uses environmentally sensitive reagents. Many techniques require extensive and tedious sample preparation steps which make the determination cumbersome and not amenable to rapid, routine analysis. Others are so inexact as to be of little value in addressing the needs of the RoHS act. A method that rapidly and accurately identifies the presence of brominated flame retardants in polymers would be a valuable addition to the art.

BRIEF DESCRIPTION OF THE DRAWINGS

The features of the invention believed to be novel are set forth with particularity in the appended claims. The invention itself however, both as to organization and method of operation, together with objects and advantages thereof, may be best understood by reference to the following detailed description of the invention, which describes certain exemplary embodiments of the invention, taken in conjunction with the accompanying drawings in which:

DETAILED DESCRIPTION

Figure 1:
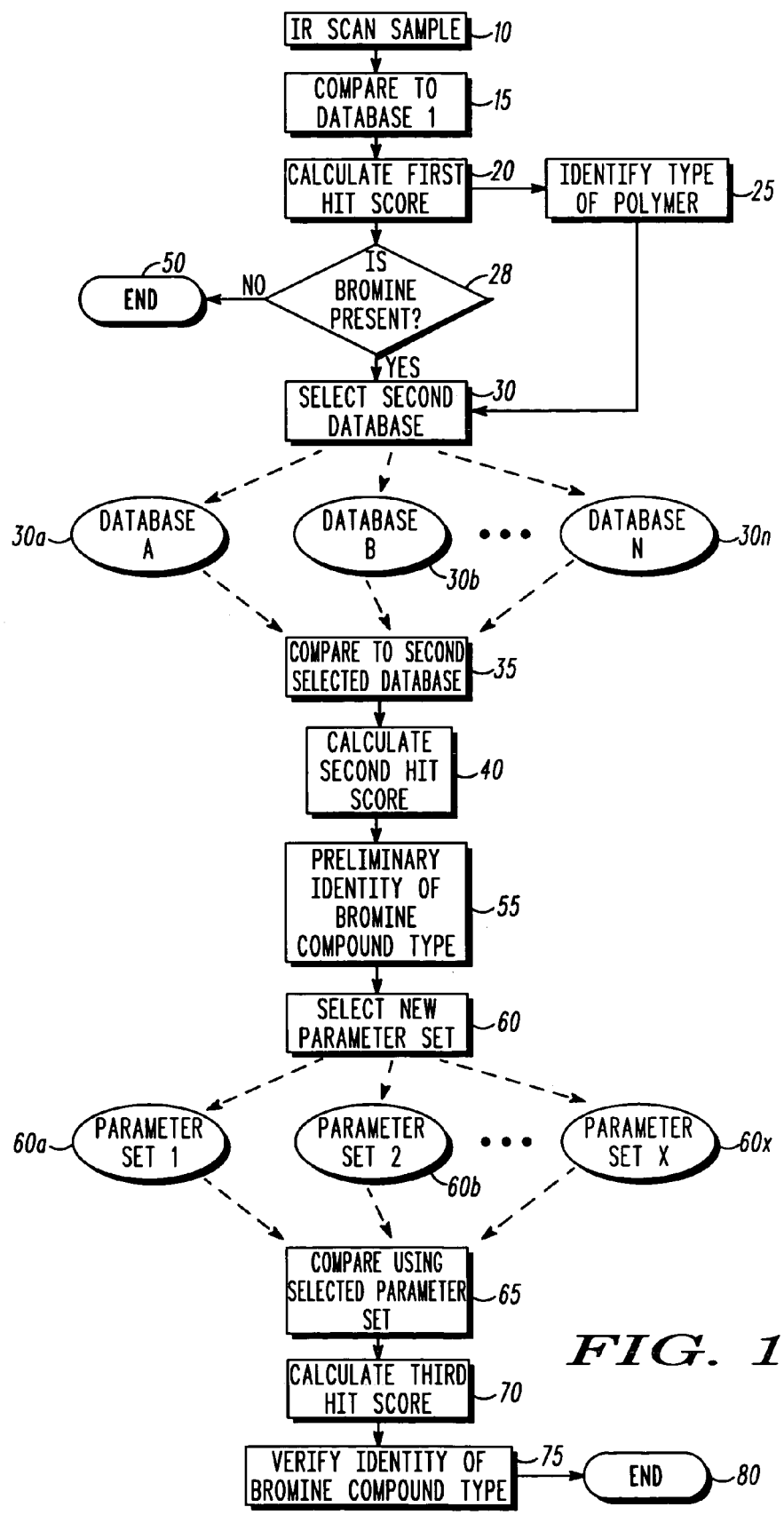
FIGS. 1-3 are flow charts depicting decision tree analysis methods consistent with certain embodiments of the present invention.

While this invention is susceptible of embodiment in many different forms, there is shown in the drawings and will herein be described in detail specific embodiments, with the understanding that the present disclosure is to be considered as an example of the principles of the invention and not intended to limit the invention to the specific embodiments shown and described. In the description below, like reference numerals are used to describe the same, similar or corresponding elements in the several views of the drawings.

Attenuated Total Reflection Fourier Transform Infrared Spectrometry (ATR-FT-IR) is used to identify polybrominated biphenyls (PBB) and polybrominated biphenyl oxides (PBDE) in polymers. Octabromodiphenyl (OBB), decabromodiphenyl (DBB), octabromodiphenyl oxide (OBDE), decabromodiphenyl oxide (DBDE), and tetrabromobisphenol A (TBBPA) are frequently used as flame retardants in engineering plastics in the electronic industry. These and other brominated flame retardants possess one or more bromine atoms and that have a high relative mass contribution of bromine to the overall molecular weight. This gives them distinct properties that aid in IR analysis. They exhibit certain characteristic absorption bands in the infrared region that makes the infrared spectrum of a plastic with brominated flame retardants substantially different from that of the non-flame retarded plastic. Moreover the bromine content directly reflects the concentration of brominated flame retardants in the plastic. Our invention leverages these phenomena to characterize real-world material samples by use of mathematical processes and a decision tree with cut off criteria that provides determination of the correct sample composition. Suitable wavelength areas (990-1050 cm−1; 1230-1480 cm−1) of the obtained attenuated total reflectance (ATR) infrared spectroscopy are selected to characterize the flame-retardant compounds that are blended into the polymer, allowing simultaneous detection using the polymer's IR spectrum. A set of sample evaluation parameters such as wavelength areas, mathematical procedures for spectra conversion, and data evaluation is presented. These include the use of spectral derivations, threshold limits for mathematical similarity assessment, and decision trees. Additionally, reference samples made by compounding commercial flame retardant standards with engineering polymers are used as reference spectra for further identification.

Referring now to FIG. 1, an infrared spectrum (IR) scan of the polymer sample in question is obtained in step 10, typically using a Fourier transform infrared (FT-IR) spectrophotometer. We find it advantageous to use the sampling technique of attenuated total reflectance (ATR) to obtain a scan directly on the sample, which eliminates the need for extensive sample preparation. To get the plastic sample ready for measurement, a piece of the polymer to be tested (for example a cellular telephone housing) with a 2×2 millimeter planar surface is cut from the larger object and put on the crystal of the ATR unit. Spectra were typically recorded in the range of 200 to 8000 cm$^{-1}$ using 15 scans per sample. The obtained digital spectrum is then compared point by point through the use of appropriately selected mathematical parameters, to a first database in step 15 in order to identify the type of polymer that is in the sample. This first comparison utilizes one of a number of commercial databases of polymers, and the result of this identification will guide the decision making process in subsequent steps. The point by point comparison of the sample spectrum to the commercial database is performed using software provided by the IR spectrophotometer manufacturer. We find that the following general types of parameters are useful in making the identification. The spectrum is mathematically transformed to the 1$^{st}$ derivative and normalized using vector normalization to make sure the spectrum is comparable to those in the database (See Equation 1).

$$x_i = \frac{y_i}{\sqrt{\sum_{j=1}^{n}(y_j)^2}} \qquad \text{Equation 1}$$

This process looks at the spectrum as being a vector with the coordinates being the data points of the spectrum. Each coordinate $y_i$ of the 1$^{st}$ derivative of the vector (Spectrum) S is divided by the value of the vector. Therefore the sum of all the normalized function values is one (the Euclidian Norm) (See Equation 2).

$$\sum_{i=1}^{n}(x_i)^2 = 1 \qquad \text{Equation 2}$$

Using the algorithms described above, the first comparison step 15 uses a commercial database to determine the main polymer in the unknown sample. The spectrum of the unknown sample is compared to each of the entries in the first database by subtracting the normalized spectral vectors. Most commercial databases contain tens of thousands of compounds, and clearly the use of digital computing techniques facilitates this comparison. Following the normalization, the vectors of the unknown sample and the selected spectrum in the database are subtracted, squared and then summed over all data points.

A first hit score is then calculated in step 20 for each spectrum compared, based on these sums, where low sum values directly correlate to high hit scores. The hit score is calculated using the formula:

Hit Score=(1−Sum value)*1000

A high hit score indicates that the two spectra are similar. Hit score values range from 0-1000, and we find that a hit score of 750 or greater is generally required to provide a reliable identification of the polymer in the unknown sample. Many software packages with today's spectrophotometers provide an analog overlay of the unknown sample with the closest matches so the human user can further verify the match. Once the base polymer or polymer blend in the sample (in this example, the cellular telephone housing) is identified in step 25, the presence or absence of a bromine compound is determined (step 28) by means of energy dispersive X-ray fluorescence spectroscopy (EDXRF), using techniques that are standard in the art. If bromine is not present, then the analysis is terminated at this point (step 50). Assuming that the presence of bromine is confirmed by EDXRF (step 28), then a second database is selected (step 30) from among a plurality of databases ($30_a$, $30_b$ ... $30_n$). The identification of the main polymer species that is present is very important, as it determines which databases and sets of parameters will be used in subsequent steps. The decision as to which of the plurality of databases to select is a function of the type of polymer identified in the sample. For example, if the polymer is found to be acrylonitrilebutadiene styrene (ABS), then a database having ABS polymers with brominated flame retardants is selected. If the polymer is found to be polycarbonate (PC), then a database having polycarbonate polymers with brominated flame retardants is selected, and so on. Each database contains a number of known, standard polymers of a single type, blended with one or more brominated flame retardants. To insure maximum accuracy, these databases were specially prepared in our laboratories by running IR spectra on highly characterized samples. In practice, a single database is selected for the next comparison step. The spectrum of the sample under test is then compared to each of the spectra in the selected database using a set of mathematical parameters (step 35) that are customized to each particular database. For example, if the polymer is found to be ABS, then certain wavelength regions are selected for comparison that have a minimum of interference with the ABS spectrum. Or, if the polymer is found to be polycarbonate, then certain wavelength regions are selected for comparison that have a minimum of interference with the polycarbonate spectrum. These regions will vary for each type of polymer tested, and generally consist of 2-8 different regions for each polymer. After comparing the test sample to each of the reference samples in the selected database using the selected set of parameters, a second set of hit scores are calculated (step 40) in a similar manner to that previously explained. Based on that second hit score, a preliminary identification of the type of brominated compound is made (step 55). Hit score values range from 0-1000, and we find that a hit score of 750 or greater is generally required to properly identify the brominated flame retardant compound in the unknown sample.

If a brominated compound is present, hit scores for one or more compounds such as PBB, PBDE, OBB, DBB, OBDE, TBBPA, and DBDE will be generated, and a preliminary assignment of the type of bromine compound is made, based on the quality of the various hit scores (step 55). At this point, we find it useful to use an additional set of parameters to check the assignment. For example, if the second set of hit scores indicates that OBDE is the flame retardant, then a third, and different, set of parameters will be used to verify that assignment.

Based on the preliminary identity of the brominated compound, a third comparison is made using a new and different set of mathematical parameters. On the surface, this step appears to be quite similar to the previous steps, and may seem redundant to the casual observer, but we find that it provides a heretofore unobtainable level of accuracy in the identification process. The decision as to which set of parameters to select (step 60) is directly related to the type of brominated compound identified in the sample. For example, if the test sample is identified as ABS polymer with PBDE brominated flame retardant, then a parameter set tailored specifically to that combination will be used for verification. Alternatively, if the test sample is identified as a polyolefin polymer with DBDE brominated flame retardant, then a parameter set tailored specifically to that combination will be used for verification, and so on. Each unique combination of polymer and brominated flame retardant has its own set of evaluation parameters (60a, 60b, . . . 60x) that includes specific wavelength regions for comparison and specific mathematical criteria. The spectrum of the sample under test is then compared to each of the spectra in the previously selected database using the newly selected set of mathematical parameters (step 65), and a third set of hit scores are calculated (step 70) in a similar manner to that previously explained. Based on the third set of hit scores, the preliminary identity of the brominated flame retardant compound made in step 55 is confirmed or denied (step 75). We find that a hit score of 750 or greater is generally required to verify the first identification, and lower hit scores are an indicator that the preliminary identification of the brominated flame retardant was probably incorrect. The analysis procedure ends at this point (step 80).

Having explained the method, we now offer a case study example by way of illustration. In this example, a cellular telephone housing made of acrylonitrilebutadiene styrene (ABS) with an octabromodiphenyl oxide (OBDE) flame retardant is analyzed. An infrared spectrum scan of the ABS/OBDE sample was obtained using the sampling technique of attenuated total reflectance in a Fourier transform infrared spectrophotometer. A piece of cellular telephone housing with a 2 ×2 millimeter planar surface was cut and placed on the crystal of the ATR unit. Spectra were typically recorded in the range of 200 to 8000 cm$^{-1}$ using 15 scans per sample. The obtained digital spectrum was then compared to reference spectra in the database by subtracting the normalized spectral vectors. Table 1 shows the data points of the original spectra and selected database spectra together with the derivatives of the spectrum in this range.

These data are then transformed according to Equation 1 to Xi. The squares of the result Xi are shown in Table 2 for each of the spectra, U, Y1 and Y2. Column 11 and 12 calculates the difference between the database spectra and the unknown spectrum.

The squares of these spectral differences are summed in Table 3.

TABLE 1

| Column 1 Data points | Column 2 Intensities (unknown Sample U) | Column 3 Intensities (spectrum 1) | Column 4 Intensities (spectrum 2) | Column 5 1st deriv. Y-U (unknown sample) | Column 6 1st deriv. Y-1 (spectrum 1) | Column 7 1st deriv. Y-2 (spectrum 2) |
|---|---|---|---|---|---|---|
| 1732 | 0.61061 | 0.52927 | 0.77990 | 0.01484 | 0.01719 | −0.00006 |
| 1728 | 0.55125 | 0.4605 | 0.74957 | 0.01442 | 0.01653 | −0.00013 |
| 1724 | 0.49525 | 0.39703 | 0.71802 | 0.01367 | 0.01502 | −0.00043 |
| 1720 | 0.44188 | 0.34032 | 0.68594 | 0.01752 | 0.01622 | −0.00105 |
| 1717 | 0.37677 | 0.28551 | 0.66249 | 0.01488 | 0.00926 | −0.00061 |
| 1713 | 0.34455 | 0.28448 | 0.66563 | 0.00117 | −0.00357 | 0.00018 |
| 1707 | 0.37885 | 0.32883 | 0.67924 | −0.00868 | −0.01256 | −0.00006 |
| 1703 | 0.42543 | 0.39972 | 0.70692 | −0.01237 | −0.01727 | −0.00089 |
| 1699 | 0.47784 | 0.467 | 0.73487 | −0.01286 | −0.02382 | −0.00257 |
| 1697 | 0.50309 | 0.52864 | 0.76978 | −0.01263 | −0.03082 | −0.00362 |

TABLE 2

| Data points | Column 8 $Xi^2$ (Unknown) | Column 9 $Xi^2$ (Y1) | Column 10 $Xi^2$ (Y2) | Column 11 Column 9 − Column 8 Difference between unknown and database spectrum 1 | Column 12 Column 10 − Column 8 Difference between unknown and database spectrum 2 |
|---|---|---|---|---|---|
| 1732 | 0.00000037 | 0.00000092 | 0.0000000448864 | 0.000350 | −0.000400 |
| 1728 | 0.00000035 | 0.00000086 | 0.0000000468013 | 0.000330 | −0.000378 |
| 1724 | 0.00000032 | 0.00000071 | 0.0000000493754 | 0.000277 | −0.000341 |
| 1720 | 0.00000052 | 0.00000082 | 0.0000000490034 | 0.000185 | −0.000501 |
| 1717 | 0.00000038 | 0.00000027 | 0.0000000096797 | −0.000095 | −0.000515 |
| 1713 | 0.00000000 | 0.00000004 | 0.0000000018287 | −0.000248 | −0.000091 |
| 1707 | 0.00000013 | 0.00000049 | 0.0000000164589 | −0.000345 | 0.000229 |
| 1703 | 0.00000026 | 0.00000093 | 0.0000000377351 | −0.000456 | 0.000315 |
| 1699 | 0.00000028 | 0.00000178 | 0.0000001166591 | −0.000803 | 0.000188 |
| 1697 | 0.00000027 | 0.00000297 | 0.0000002378851 | −0.001204 | 0.000033 |

TABLE 3

| Data points | Column 13 Column Squared Spectral Differences $(Y1-U)^2$ | Column 14 Column Squared Spectral Differences $(Y2-U)^2$ |
|---|---|---|
| 1732 | 3.03E−13 | 1.08E−13 |
| 1728 | 2.52E−13 | 9.38E−14 |
| 1724 | 1.51E−13 | 7.18E−14 |
| 1720 | 9.12E−14 | 2.23E−13 |
| 1717 | 1.16E−14 | 1.34E−13 |
| 1713 | 1.41E−15 | 2.46E−19 |
| 1707 | 1.34E−13 | 1.24E−14 |
| 1703 | 4.54E−13 | 4.93E−14 |
| 1699 | 2.23E−12 | 2.69E−14 |
| 1697 | 7.30E−12 | 1.09E−15 |
| SUM | 1.09E−11 | 7.21E−13 |

TABLE 4

Parameter set 1

| | |
|---|---|
| Search algorithm: | Spectral correlation |
| Normalization: | Vector-normalization |
| Derivation: | 1st grade |
| Areas searched: | Name: ABS3 |
| | 980-1015 cm−1 |
| | 1047-1051 cm−1 |
| | 1235-1340 cm−1 |
| | 1472-1476 cm−1 |
| Database: | ABS-Database |

As the sum in column 14 is smaller than the sum in column 13 over the range observed, database spectrum 2 is a better match to the unknown than database spectrum 1, and the polymer was identified as ABS, and the ABS database and the parameters as shown in Table 4 were selected for the next step.

Vector normalization was used, because larger differences were obtained for the hit quality in comparison to the Min-Max normalization. Using the 1st Derivation gave better search results than with the other parameters. Table 5 shows the hit score results of the spectral search using the parameters from Table 4. A 100% similarity of spectra correlates to a hit quality of 1000.

TABLE 5

| Sample No. | FSM | Hit quality of the correct assignment | Hit quality of the first incorrect assignment |
|---|---|---|---|
| 2698 + OBDE_2 | OBDE | 915 | 402 |
| 3095 + OBDE_2 | OBDE | 875 | 343 |
| 3257_2 | OBDE | 873 | 310 |
| 1887 | Non extractable compound | 884 | 478 |
| 2835a | TBBPA | 805 | 399 |
| 2850 | none | 664 | 410 |
| 3095 + TBBPA | TBBPA | 871 | 266 |
| 3095 | none | 720 | 535 |
| 3105 | none | 705 | 567 |
| 3265a | TBBPA | 687 | 462 |
| 3368a | TBBPA | 797 | 338 |
| 3750a_2 | Non extractable compound | 712 | 472 |
| ERL23 | none | 857 | 707 |

All samples for the test set were correctly assigned with respect to the flame retardant content with a hit quality score of higher than 800 (80%).

A second set of parameters was then used to check the correct assignment. For example if parameter set 1 revealed TBBPA as the flame retardant, parameter set 2 (specific for TBBPA) would be used to confirm it. Also if OBDE was identified using parameter set 1, then parameter set 3 should be used to confirm the selection. Table 6 depicts two particular parameter sets (Sets 2 and 3) employed for the confirmation of flame retardant assignments for ABS polymers.

TABLE 6

Parameter set 2 (ABS-TBBPA confirmation)

| | |
|---|---|
| Search algorithm: | Spectral correlation |
| Normalization: | Vector-normalization |
| Derivation: | 1st grade |
| Areas searched: | Name: ABS_TBBPA |
| | 860-895 cm−1 |
| | 930-945 cm−1 |
| Database: | ABS-Database |

Parameter set 3 (for ABS-OBDE confirmation)

| | |
|---|---|
| Search algorithm: | Spectral correlation |
| Normalization: | Vector-normalization |
| Derivation: | 1st grade |
| Areas searched: | Name: ABS_OBDE |
| | 1040-1060 cm−1 |
| | 1105-1120 cm−1 |
| | 1200-1215 cm−1 |
| | 1230-1270 cm−1 |
| Database: | ABS-Database |

TABLE 7

| Sample Number | Flame Retardant | Hit quality of the correct assignment | Hit quality of the first incorrect assignment |
|---|---|---|---|
| 2835a | TBBPA | 974 | 508 |
| 3095 + TBBPA | TBBPA | 961 | 469 |
| 3265a | TBBPA | 959 | 527 |
| 3368a | TBBPA | 962 | 510 |
| 2698 + OBDE_2 | OBDE | 931 | 314 |
| 3095 + OBDE_2 | OBDE | 937 | 277 |
| 3257_2 | OBDE | 955 | 182 |

The power of our decision tree techniques is shown in Table 7, where the results of using parameter sets 2 and 3 on seven (7) different polymer samples are displayed. High hit scores of over 900 occurred in all samples, indicating that the quality of the brominated compound assignment was very high, nearly perfect. Three of the seven samples were known mixtures used as blind samples to verify the accuracy of the test. The flame retardant type is confirmed for all samples.

Figure 2:
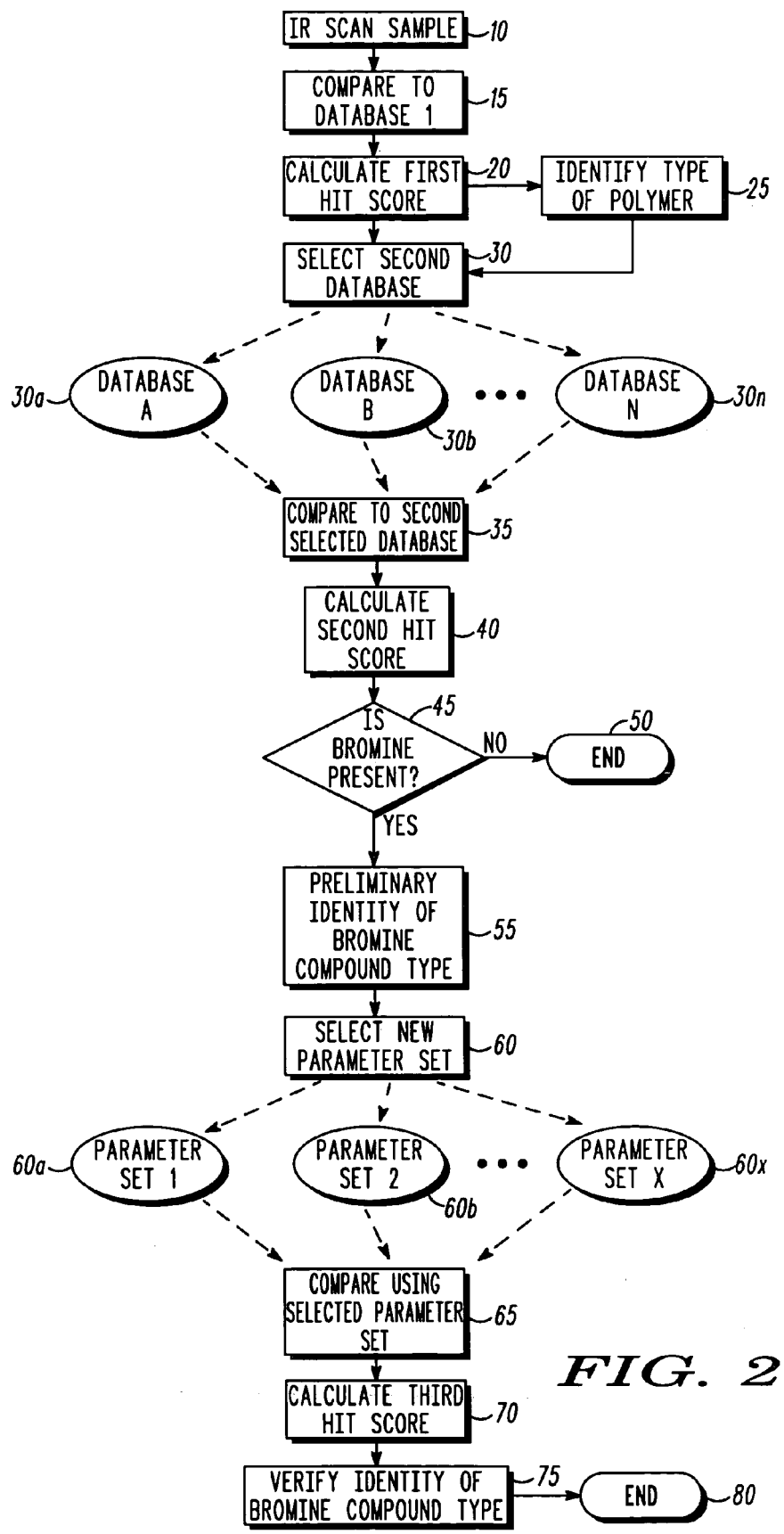

In an alternate embodiment of the invention shown in FIG. 2, an infrared spectrum (IR) scan of the polymer sample in question is obtained in step 10, typically using ATR FT-IR by placing a piece of the polymer to be tested on the crystal of the ATR unit. Spectra are typically recorded in the range of 200 to 8000 cm$^{-1}$ using 15 scans per sample. The obtained digital spectrum is then compared point by point through the use of appropriately selected mathematical parameters, to a first database in step 15 in order to identify the type of polymer that is in the sample. This first comparison utilizes one of a number of commercial databases of polymers, and the result of this identification will guide the decision making process in subsequent steps. A first set of hit scores are then calculated in step 20 for each spectrum compared, and the identity of the base polymer or polymers is determined based on the hit scores. Once the base polymer or polymer blend in the sample is identified in step 25, a second database is selected (step 30) from among a plurality of databases (30$_a$, 30$_b$ . . . 30$_n$). The identification of the main polymer species that is present is very important, as it determines which databases and sets of parameters will be used in subsequent steps. The decision as to which of the plurality of databases to select is a function of the type of polymer identified in the sample. For example, if the polymer is found to be ABS, then a database having ABS polymers with brominated flame retardants is selected, and so on in the case of the other types of polymers. Each database contains a number of known, standard polymers of a single type, blended with one or more brominated flame retardants. The spectrum of the sample under test is then compared to each of the spectra in the selected database using a set of mathematical parameters (step 35) that are customized to each particular database. For example, if the polymer is found to be ABS, then certain wavelength regions are selected for comparison that have a minimum of interference with the ABS spectrum. These regions will vary for each type of polymer tested, and generally consist of 2-8 different regions for each polymer. After comparing the test sample to each of the reference samples in the selected database using the selected set of parameters, a second hit score is calculated (step 40) in a similar manner to that previously explained. Based on that second hit score, the presence or absence of a brominated flame retardant compound is established (step 45). Hit score values range from 0-1000, and we find that a hit score of 750 or greater is generally required to establish the presence of a brominated flame retardant compound in the unknown sample. Lower hit scores are an indicator that a brominated flame retardant is probably not present, and the analysis procedure would end at this point (step 50).

If high hit scores indicate that a brominated compound is present, then a preliminary identity of the type of brominated compound is made at this time. If a brominated compound is present, hit scores for one or more compounds such as PBB, PBDE, OBB, DBB, OBDE, TBBPA, and DBDE will be generated, and a preliminary assignment of the type of bromine compound is made, based on the quality of the various hit scores (step 55). At this point, we find it useful to use a third set of parameters to check the assignment. For example, if the second set of hit scores indicates that OBDE is the flame retardant, then a third, and different, set of parameters will be used to verify the assignment. Based on the preliminary identity of the brominated compound, a third comparison is made using a new and different set of mathematical parameters. The decision as to which set of parameters to select (step 60) is directly related to the type of brominated compound identified in the sample. For example, if the test sample is identified as ABS polymer with PBDE brominated flame retardant, then a parameter set tailored specifically to that combination will be used for verification, and so on. Each unique combination of polymer and brominated flame retardant has its own set of evaluation parameters (60a, 60b, . . . 60x) that includes specific wavelength regions for comparison and specific mathematical criteria. The spectrum of the sample under test is then compared to each of the spectra in the previously selected database using the newly selected set of mathematical parameters (step 65), and a third set of hit scores are calculated (step 70) in a similar manner to that previously explained. Based on the third set of hit scores, the preliminary identity of the brominated flame retardant compound made in step 55 is confirmed or denied (step 75). We find that a hit score of 750 or greater is generally required to verify the first identification, and lower hit scores are an indicator that the preliminary identification of the brominated flame retardant was probably incorrect. The analysis procedure ends at this point (step 80).

Figure 3:
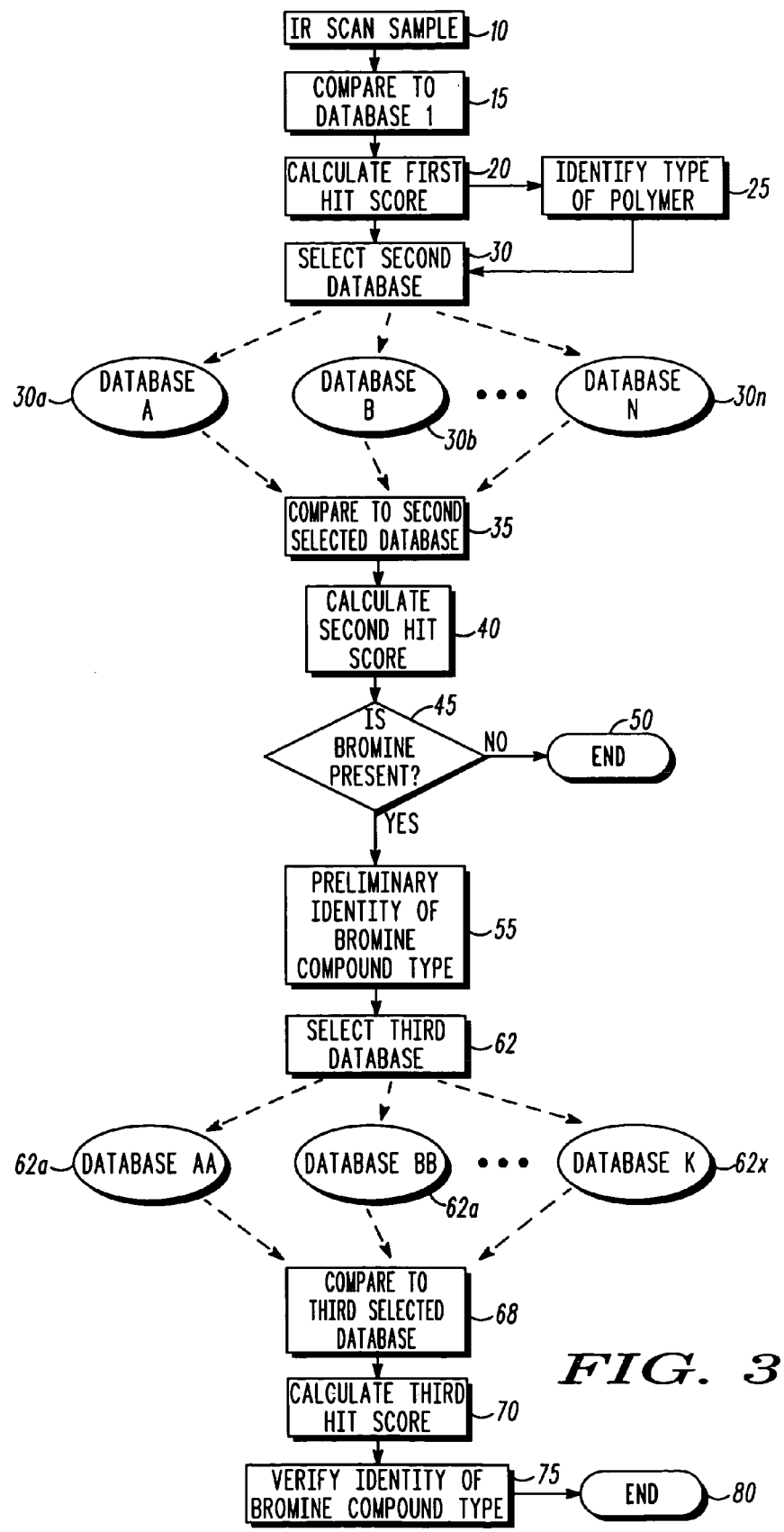

In still another embodiment depicted in FIG. 3, after the preliminary identification of the bromine compound is made in step 55, a third database is selected in step 62 from a plurality of databases (62a, 62b, . . . 62x). Each of these databases has associated with it a unique set of evaluation parameters for the various combinations of flame retardant/polymer. The spectrum of the unknown sample is then compared to the selected third database using the new parameter set (step 68), and the third set of hit scores are generated (step 70). Hit scores of 750 or greater generally substantiate the first identification, and lower hit scores are an indicator that the preliminary identification of the brominated flame retardant was probably incorrect. The analysis procedure ends at this point (step 80).

In summary, without intending to limit the scope of the invention, identification of brominated flame retardant additives such as octabromodiphenyl, decabromodiphenyl, octabromodiphenyl oxide, decabromodiphenyl oxide, and tetrabromobisphenol A in polymers such as acrylonitrilebutadiene styrene, polyolefins, polycarbonates, polyethylene terephthalate, epoxy, polyester, polyimide, and blends thereof commonly used to fabricate radio housings, printed circuit boards and battery packages, using infrared spectroscopy according to a method consistent with certain embodiments of the invention, can be carried out by a decision tree methodology that utilizes unique databases and evaluation parameters specific to each combination of polymer and flame retardant. While the invention has been described by citing specific details and parameters used in actual analyses, it is to be understood that these are offered by way of example, and not by way of limitation, and variation from these settings and values may most certainly occur and still fall within the scope and spirit of the invention. It is evident that many alternatives, modifications, permutations and variations will become apparent to those of ordinary skill in the art in light of the foregoing description. Accordingly, it is intended that the present invention embrace all such alternatives, modifications and variations as fall within the scope of the appended claims.

What is claimed is:

1. A method for identifying brominated flame retardants in a polymer sample, comprising:
   a) obtaining an infrared spectrometry scan of the polymer sample;
   b) using a first set of parameters, comparing the obtained infrared spectrometry scan to scans in a first database stored on a computer readable medium, and calculating a first hit score;
   c) using the first hit score, selecting a second database$_{(n)}$ stored on a computer readable medium and a parameter set$_{(n)}$, where n is an index;
   d) using the selected parameter set$_{(n)}$, comparing the obtained infrared spectrometry scan to scans in the selected database$_{(n)}$, and calculating a second hit score;
   e) using the second hit score, making a preliminary identification of the brominated flame retardant;
   f) based on the preliminary identification, selecting a parameter set$_{(k)}$ where k is an index not equal to n;
   g) using the selected parameter set$_{(k)}$, comparing the obtained infrared spectrometry scan to scans in the selected database$_{(n)}$, and calculating a third hit score; and
   h) based on the third hit score, confirming the identity of the brominated flame retardant in the polymer sample.

2. The method of claim 1, wherein the calculated first, second, and third hit scores are output in human readable form.

3. The method of claim 1, wherein the polymer sample is selected from the group consisting of acrylonitrilebutadiene styrene, polyolefin, polycarbonate, polyethylene terephthalate, epoxy, polyester, and polyimide.

4. The method of claim 1, wherein the polymer sample is a radio housing, a printed circuit board, or a battery package.

5. A method for identifying brominated flame retardants in a polymer sample, comprising:
   a) obtaining an infrared spectrometry scan of the polymer sample;
   b) using a first set of parameters, comparing the obtained infrared spectrometry scan to a first database stored on a computer readable medium, and calculating a first hit score;
   c) using the first hit score, selecting a second database$_{(n)}$ stored on a computer readable medium and a parameter set$_{(n)}$, where n is an index;
   d) using the selected parameter set$_{(n)}$, comparing the obtained infrared spectrometry scan to scans in the selected database$_{(n)}$, and calculating a second hit score;
   e) using the second hit score, determining if the brominated flame retardant is present;
   f) if the brominated flame retardant is present, making a preliminary identity of the compound type;
   g) based on the preliminary identity, selecting a parameter set$_{(k)}$ where k is an index not equal to n;
   h) using the selected parameter set$_{(k)}$, comparing the obtained infrared spectrometry scan to scans in the selected database$_{(n)}$, and calculating a third hit score; and
   i) based on the third hit score, confirming the identity of the brominated flame retardant in the polymer sample.

6. The method of claim 5, wherein the calculated first, second, and third hit scores are output in human readable form.

7. The method of claim 5, wherein the database$_{(n)}$ comprises synthetically prepared reference samples.

8. The method of claim 5, wherein the database$_{(k)}$ comprises synthetically prepared reference samples.

9. The method of claim 5, wherein the polymer sample is selected from the group consisting of acrylonitrilebutadiene styrene, polyolefins, polycarbonates, polyethylene terephthalate, epoxy, polyester, and polyimide.

10. The method of claim 5, wherein the polymer sample is a radio housing, a printed circuit board, or a battery package.

11. A method for identifying brominated flame retardants in a polymer sample, comprising:
   a) obtaining an infrared spectrometry scan of the polymer sample;
   b) using a first set of parameters, comparing the obtained infrared spectrometry scan to scans in a first database stored on a computer readable medium, and calculating a first hit score;
   c) using the first hit score, selecting a second database$_{(n)}$ stored on a computer readable medium and a parameter set$_{(n)}$, where n is an index;
   d) using a parameter set$_{(n)}$, comparing the obtained infrared spectrometry scan to scans in the selected database$_{(n)}$, and calculating a second hit score;
   e) using the second hit score, selecting a database$_{(k)}$ where k is an index not equal to n;
   f) using the selected parameter set$_{(k)}$, comparing the obtained infrared spectrometry scan to scans in the selected database$_{(k)}$, and calculating a third hit score; and
   g) based on the second and third hit scores, deciding if a brominated flame retardant is present in the polymer sample.

12. The method of claim 11, further comprising a final step of identifying the brominated flame retardant.

13. The method of claim 11, wherein the calculated first, second, and third hit scores are output in human readable form.

14. The method of claim 11, wherein the polymer sample is selected from the group consisting of acrylonitrilebutadiene styrene, polyolefins, polycarbonates, polyethylene terephthalate, epoxy, polyester, and polyimide.

15. The method of claim 11, wherein the polymer sample is a radio housing, a printed circuit board, or a battery package.

16. A method for identifying brominated compounds in a polymer sample, comprising:
   a) obtaining an infrared spectrometry spectrum of the polymer sample;
   b) comparing the obtained infrared spectrometry spectrum to spectra in a first database stored on a computer readable medium to identify the type of polymer in the polymer sample;
   c) selecting a second database stored on a computer readable medium and a first parameter set according to the identified type of polymer; and
   d) using the first parameter set, comparing the obtained infrared spectrometry spectrum to spectra in the second database to make a preliminary identification of the brominated compound.

17. A method in accordance with claim 16, further comprising:
   e) selecting a second parameter set according to the preliminary identification; and
   f) using the second parameter set, comparing the obtained infrared spectrometry spectrum to spectra in the second database to confirm the preliminary identification of the brominated compound in the polymer sample.

* * * * *